United States Patent [19]
Abdel-Mottaleb

[11] Patent Number: 5,768,333
[45] Date of Patent: Jun. 16, 1998

[54] MASS DETECTION IN DIGITAL RADIOLOGIC IMAGES USING A TWO STAGE CLASSIFIER

[75] Inventor: Mohamed S. Abdel-Mottaleb, Ossining, N.Y.

[73] Assignee: Philips Electronics N.A. Corporation, New York, N.Y.

[21] Appl. No.: 758,651

[22] Filed: Dec. 2, 1996

[51] Int. Cl.$^6$ .................................................... A61B 6/00
[52] U.S. Cl. .............................................. 378/37; 378/62
[58] Field of Search ................................... 378/37, 62

[56] References Cited

U.S. PATENT DOCUMENTS

| | | | |
|---|---|---|---|
| 4,236,078 | 11/1980 | Kotera et al. | 250/363 R |
| 5,289,374 | 2/1994 | Doi et al. | 364/413.13 |
| 5,365,429 | 11/1994 | Carman | 364/413.13 |
| 5,537,485 | 7/1996 | Nishikawa et al. | 382/130 |
| 5,572,565 | 11/1996 | Abdel-Mottaleb | 378/37 |
| 5,579,360 | 11/1996 | Abdel-Mottaleb | 378/37 |
| 5,615,243 | 3/1997 | Chang et al. | 378/37 |

OTHER PUBLICATIONS

"Evaluation of Stellate Lesion Detection in a Standard Mammogram Data Set", W. Philip Kegelmeyer Jr., Sandia National Laboratories, International Journal of Pattern Recognition and Artificial Intelligence vol. 7, No. 6 (1993) 1477–1492.

"Computer–Aided Classification of Mammographic Masses and Normal Tissue: Linear Discriminant Analysis in Texture Feature Space", Phys. Med. Biol. 40 (1995) 857–876, U.K.

"Algorithms for Graphics and Image Processing", Theo Pavlidis, Bell Laboratories, Computer Science Press, 1982, pp. 116–120.

"Clustering Algorithms", John A. Hartigan, Department of Statistics Yale University, John Wiley & Sons, 1975, pp. 84–111.

"Computerized Detection of Clustered Microcalcifications in Digital Mammograms using a Shift–Invariant Artificial Neural Network", Wei Zhang, Kunio Doi, Maryellen L. Giger, Yuzheng Wu, Robert M. Nishikawa, and Robert A. Schmidt, Med. Phys. 21 (4) Apr. 1994, pp. 517–523.

"Textured Image Segmentation", by Kenneth Ivan Laws, Jan. 1980, Engineering IPI (Image Processing Institute), USCIPI Report 940.

*Primary Examiner*—David P. Porta
*Assistant Examiner*—David Vernon Bruce
*Attorney, Agent, or Firm*—Jack D. Slobod

[57] ABSTRACT

A computer-implemented method of identifying suspect masses in digital radiologic images and a system for computer-aided diagnosis of such images in which the images are thresholded at a large number of threshold levels to discriminate spots and a two stage classifier is applied to the spots. The first classification stage applies multiple rules predetermined from a training set of images, to a relatively computationally inexpensive set of initial features, namely area, compactness, eccentricity, contrast, and intensity variance for each spot. More computationally expensive features, namely edge orientation distribution and texture features, are computed only for spots that are accepted by the first classification stage to points for these spots in an expanded feature space. In the second classification stage, these points are classified as true positives or false positives in dependence on which mean of a plurality of clusters of true positives and a plurality of clusters of false positives, predetermined from the training set, is nearest in Mahalanobis distance.

20 Claims, 6 Drawing Sheets

E5L5

| -1 | -4 | -6 | -4 | -1 |
|---|---|---|---|---|
| -2 | -8 | -12 | -8 | -2 |
| 0 | 0 | 0 | 0 | 0 |
| 2 | 8 | 12 | 8 | 2 |
| 1 | 4 | 6 | 4 | 1 |

| 1 | -4 | 6 | -4 | 1 |
|---|---|---|---|---|
| -4 | 16 | -24 | 16 | -4 |
| 6 | -24 | 36 | -24 | 6 |
| -4 | 16 | -24 | 16 | -4 |
| 1 | -4 | 6 | -4 | 1 |

| 1 | 0 | -2 | 0 | 1 |
|---|---|---|---|---|
| 2 | 0 | -4 | 0 | 2 |
| 0 | 0 | 0 | 0 | 0 |
| -2 | 0 | 4 | 0 | -2 |
| -1 | 0 | 2 | 0 | -1 |

FIG. 6C

| -1 | 0 | 2 | 0 | -1 |
|---|---|---|---|---|
| -4 | 0 | 8 | 0 | -4 |
| -6 | 0 | 12 | 0 | -6 |
| -4 | 0 | 8 | 0 | -4 |
| -1 | 0 | 2 | 0 | -1 |

| 1 | 4 | 6 | 4 | 1 |
|---|---|---|---|---|
| 4 | 16 | 24 | 16 | 4 |
| 6 | 24 | 36 | 24 | 6 |
| 4 | 16 | 24 | 16 | 4 |
| 1 | 4 | 6 | 4 | 1 |

MASS DETECTION IN DIGITAL RADIOLOGIC IMAGES USING A TWO STAGE CLASSIFIER

RELATED APPLICATIONS

This application is related in subject matter to the following prior commonly owned application and patents by the same inventor as this application, which are incorporated herein by reference:

1) U.S. application Ser. No. 08/699,182, filed Aug. 19, 1996, entitled "MASS DETECTION IN DIGITAL X-RAY IMAGES USING MULTIPLE THRESHOLDS TO DISCRIMINATE SPOTS", which is a continuation of U.S. application Ser. No. 08/274,939, filed Jul. 14, 1994 and now abandoned;

2) U.S. Pat. No. 5,572,565, issued Nov. 5, 1996 entitled "AUTOMATIC SEGMENTATION, SKINLINE AND NIPPLE DETECTION IN DIGITAL MAMMOGRAMS";

3) U.S. Pat. No. 5,579,360, about to issue on Nov. 26, 1996 entitled "MASS DETECTION BY COMPUTER USING DIGITAL MAMMOGRAMS OF THE SAME BREAST TAKEN FROM DIFFERENT VIEWING DIRECTIONS".

BACKGROUND OF THE INVENTION

1. Field of the Invention

The present invention relates generally to methods of and systems for computer-aided diagnosis of radiologic images which are originally in, or are converted into, digital form. In its more particular respects, the present invention relates to identification of spots that may correspond to tumors using a two stage classification process in which a plurality of feature measures of extracted spots are calculated, and in a first classification stage, candidate suspect masses are identified based on the calculated feature measures. Then in a second classification stage so-called "true positives" are identified from among the candidate suspect masses, thereby rejecting so called "false positives". The invention is particularly pertinent to Computer-Aided Diagnosis of Mammogram (CADM) but is also useful with respect to computer-aided diagnosis of other common radiologic images, for example, chest X-rays.

2. Description of the Related Art

A method of this general type is known from U.S. Pat. No. 5,289,374.

Early detection of breast cancer, the second most common cancer in women in the United States, can significantly increase the chances of survival. Such early detection requires the taking and reading by radiologists or mammographers of a large number or periodic screening mammograms. Both the number of mammogram to be interpreted and the difficulty of identifying masses and clusters of microcalcifications therein, which are potential signs of malignancy, motivate developments in Computer-Aided Diagnosis of Mammograms (CADM) to at least mark suspect areas to aid in the reading. There are related needs with regard to the detection of lung nodules in a similarly large number of chest radiographs.

Digital radiologic images suitable for computer-aided diagnosis may be obtained by scanning film taken by conventional X-ray equipment or by utilizing other X-ray detector types that produce electronic image signals that may be directly digitized without the necessity of producing a film intermediate. These detector types include X-ray image intensifier/camera chain, photostimuable phosphor plate/laser readout (see U.S. Pat. No. 4,236,078), and selenium plate/electrometer readout technologies. Such technologies are progressing in their spatial resolution and contrast sensitivities achieved and the latter two, particularly, may soon find widespread use for mammographic and chest radiographic applications.

In the prior art such as the cited U.S. Pat. No. 5,289,374, it is known to calculate a variety of feature measures of extracted spots relating to size, shape, edge gradient and/or contrast to perform a classification based on previously acquired knowledge as to ranges or thresholds for such feature measures or combinations thereof typically associated with candidate suspect masses and/or true positives.

In addition to the aforementioned, from Chan et al., "Computer-aided classification of mammographic masses and normal tissue; linear discriminant analysis in texture feature space", Phys. Med. Biol. 40 (1995) 857–876, it in known to use a plurality of texture features to distinguish between masses and normal breast parenchyma in a data set of square regions of the same fixed size in digital mammograms.

While much research is ongoing in CADM, the combination of an acceptably high rate of detection of actual true positives, and an acceptably low number of false positive detections per image, has proved illusive.

It is an object of the present invention to provide a method of and system for computer-aided detection of suspect masses in radiologic images which has a high detection rate of actual true positives and a low number of detections of false positives per image. It is further desired in order to provide such results in a sufficiently short processing time that the detection method have at least two stages of classification such that the calculation of those feature measures which are computationally expensive to calculate is deferred until after a first coarse stage of classification in which candidate suspect masses are identified using an initial set of feature measures, corresponding to an initial multi-dimensional feature space. Then in a second or final stage of classification, further computationally expensive feature measures are calculated only with regard to the determined candidate suspect masses to identify the true positives therein in an augmented or expanded feature space having more dimensions than the initial feature space.

After a radiologic image to be read has been obtained from an imaging apparatus, and if necessary, converted into digital form, an overall region of interest is identified by an automatic segmentation specific to the type of radiologic image e.g. to extract the breast from background in a mammogram. Then spots or "connected components" are extracted by thresholding the image at each gray level in a relatively large range of gray levels (in excess of 20 and typically approximately 50 consecutive gray levels) which are determined from a histogram of gray levels. Each spot discriminated at a gray level in the range is extracted. The large number of gray levels is used in order that even a spot which is discriminated as an island at only one threshold level within the range of gray levels will be extracted.

Prior to entering upon the first stage of classification, the initial set of feature measures, namely, area, compactness, eccentricity, contrast and intensity variance, is calculated for each extracted spot. The initial set of feature measures is used by the first stage of classification to identify candidate suspect masses.

Those candidate suspect masses which have been identified or accepted in the first classification stage are applied to a second classification stage wherein each candidate suspect mass is classified as either a true positive or a false positive. Prior to doing this, the initial set of feature measures is augmented by more computationally expensive feature measures, in particular edge orientation variance and so-called Laws texture features, to form an expanded set of feature measures.

In accordance with the present invention, the initial stage of classification is multiple-rule-based, which rules are devised in a training phase from a training set of radiographs in which true positives or roi's nave been marked by a radiologist or mammographer. An important aspect of the present invention is that the final stage of classification is based on comparison of the location in expanded feature space of the vector of expanded feature measures of a candidate spot with locations developed from mapping both "true positives" and "false positives" in expanded feature space in a training phase for the second stage of classification.

Key aspects of the present invention result from a recognition that suspect masses correspond to points in feature space which are distributed in a plurality of clusters or subsets.

With respect to the multiple-rule-based first classification stage, in the training phase an individual rule is devised for each cluster and in the operational phase an extracted spot is accepted as a candidate suspect mass if it passes any individual rule.

The second classification stage is trained in a training phase in which all spots from all images of the training set which pass the first stage of classification are segmented based on the markings of the radiologist into true positives and false positives. The true positives are clustered into a plurality of clusters in expanded feature space and the false positives are separately clustered into a plurality of clusters in expanded feature space. The means and covariance matrices for each of the clusters are then determined.

In the operational phase of the second classification stage, a candidate suspect mass is classified in dependence upon which mean of a cluster is nearest in Mahalanobis distance. If the nearest cluster is a true positive, then the candidate suspect mass is classified as a true positive, and is accepted. Otherwise, the candidate suspect mass is classified as a false positive and is rejected.

The present invention provides an extremely robust computer-aided diagnosis method which testing on mammograms has indicated a detection rate in excess of 90% and less than 3 false positive detections per image, on average.

BRIEF DESCRIPTION OF THE DRAWING

Other objects, features and advantages of the present invention will become apparent upon perusal of the following detailed description when taken in conjunction with the appended drawing, wherein;

FIGS. 6A through 6E show so-called Laws texture kernels used in calculating feature measures for the second classification stage of FIG. 2.

DETAILED DESCRIPTION OF THE PREFERRED EMBODIMENTS

Figure 1:
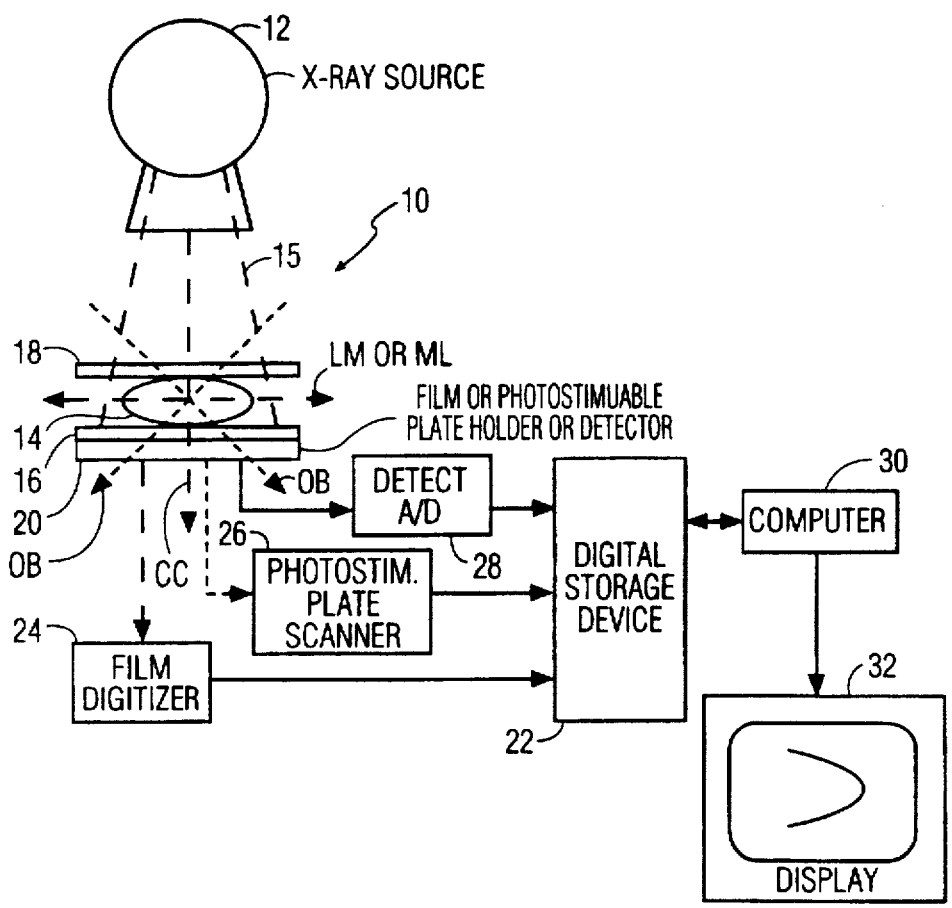
FIG. 1 is a schematic diagram of a computer-aided system in accordance with the invention for taking and processing mammograms.

Referring first to FIG. 1 of the drawing, there is shown a computer-aided mammography system 10, with its mammogram taking parts arranged for a cranio-caudal (CC) view, including an X-ray source 12 directed to irradiate a breast 14 of a standing subject with an X-ray beam 15. The breast 14 is received and compressed between generally planar lower and upper members 16, 18, using a predetermined compression force or weight. Below lower member 16 is a two-dimensional X-ray detector means 20 for detecting within a rectangular field of pixels, the X-ray radiation passing through breast 14 and its immediate external surround. X-ray detector means 20 is alternatively a film or a photostimuable phosphor image plate received in a holder, or a selenium plate/electrometer readout detector. An X-ray image intensifier/camera chain is also a suitable detector means. The X-ray source 12, plates 14 and 16 and detector means 20 may be rotated an a unit about transverse axis A to receive and irradiate breast 14 along any of the viewing directions labeled in FIG. 1 as CC (cranio-caudal), LM or ML (latero-medial or medial-lateral) and OB (oblique).

Whichever detector means 20 type is used, ultimately there is a two-dimensional array of digital pixels, representing the mammogram X-ray projection image, stored as an image file in a digital storage device 22 which may comprise a RAM, hard disk, magneto-optical disk, WORM drive, or other digital storage means. When film is used, it is developed and then scanned in a digitizer 24. Today, films may be digitized to 100 micron spatial resolution, yielding typical images ranging in size from 1672×2380 to 2344×3016 pixels, each up to 12 bit intensity resolution. When a photostituable plate is used, it is scanned by a laser in scanner 26 yielding a similar image size and typically 10 bit intensity resolution. Lastly, when a detector such as a selenium plate/electrometer readout device is utilized, it directly produces analog electrical signals that are converted to digital form by its analog to digital converter 28.

The two-dimensional array of digital pixels stored in device 22, representing the mammogram, is processed by computer workstation 30 to mark or enhance features of interest in the mammogram, including any identified suspect masses or clusters of microcalcifications, and display the resultant processed mammogram on display device 32, such as a CRT monitor. It should be understood that the various steps after the actual taking of the mammogram need not necessarily follow immediately thereafter and need not be at the same location as the taking of the mammogram.

As a preliminary step in the processing, the stored mammogram may be reduced in resolution, spatially by a suitable median filter, and/or in amplitude by truncation, to an image on the order of 500,000 to 2,500,000 pixels and 8 bit to 10-bit intensity resolution consistent with the spatial and gray scale resolution of the monitor. In particular, I have found that square pixels of 400 microns on a side and 256 gray levels per pixel give acceptable results.

In the processing to mark or enhance features, the mammogram is segmented into foreground, corresponding to the breast, and background, corresponding to the external surround of the breast and the skinline is detected in the course of this segmentation. The segmentation allows background to be eliminated from the search for features of interest, such as masses or clusters of microcalcifications, to be marked or enhanced. The segmentation may be performed by the method described in the aforementioned commonly owned U.S. Pat. No. 5,572,565. The identification of suspect clusters of microcalcifications is described in U.S. Pat. No. 5,365,429 entitled "Computer Detection of Microcalcifications in Mammograms", which is also assigned to the same assignee as the present invention.

Now referring to the flowchart shown in FIG. 2, the identification of suspect masses in a two-dimensional mammogram projection image will be described. It is assumed that as referred to heretofore, the original mammogram has been reduced in spatial resolution to about 250,000 pixels (e.g. 480×520) to form input digital radiologic image 34. Then, in step 36, segmentation is performed by skinline detection so that each pixel in the background has been removed from further consideration, a histogram of the gray values or the pixels in the foreground is calculated, and a relevant interval of gray levels for thresholding is determined from the histogram.

Figure 3:
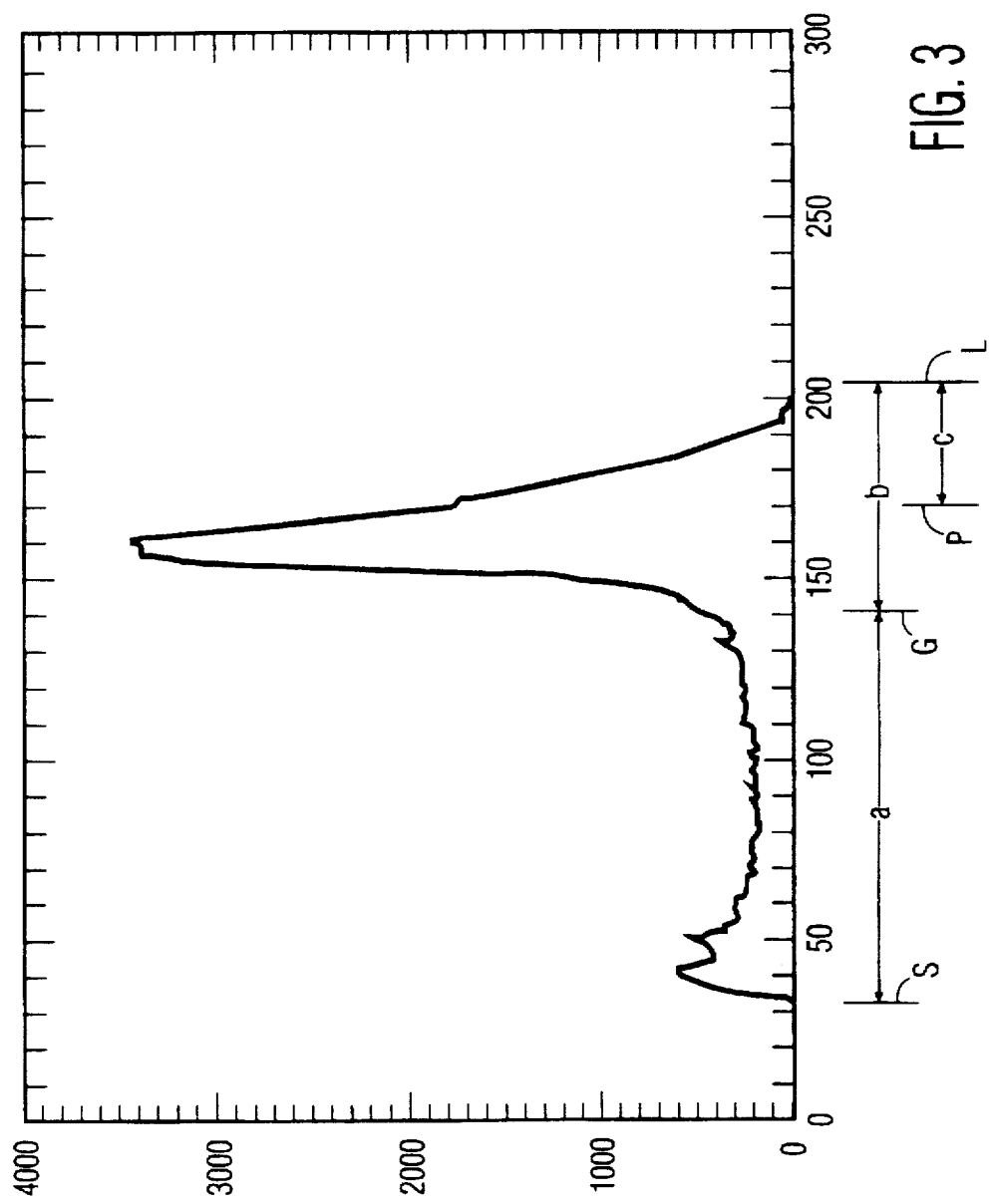
FIG. 3 is a histogram of the gray values of the pixels of a mammogram used to determine an interval of gray levels in a step of FIG. 2.

A typical histogram is shown in FIG. 3 and is seen to be subdividable into an interval "a" from the smallest gray level S in the histogram to a gray level G, which interval corresponds to the skin, and a narrower interval "b" from level G to the largest gray level L in the histogram, which interval correspond to the interior of the breast. Interval "a" has a substantially low number of pixels at each gray level while interval "b" has a relatively high peak with steep sides. The interval "b" is chosen as the relevant interval of gray levels for thresholding. Gray level G is chosen such that interval "b" twice the interval "c" between gray level L and the gray level P at the peak of the histogram.

In accordance with the invention, each gray level in interval "b" is used as a threshold. Typically, in a 256 gray level image interval "b" contains at least 20 twenty gray levels, and often more than 50. In step 38, conveniently, these gray levels are successively used as a current threshold level in either smallest to largest, or largest to smallest, order to threshold the image. At each current threshold level, a binary image, or a gray scale image whose pixels having an intensity less than the threshold level are assigned the value zero.

In step 40, spots referred to as "connected components" (CC's) are extracted from the thresholded image. Each connected component is a set of pixels having non-zero values, in which any two pixels of the set are ultimately connected to each other via a run of adjacent pixels in the set. These sets are identified conveniently by the following phases: a) generating a Line-Adjacency Graph (LAG), b) scanning the LAG to determine the number of different connected components (CC's), and c) again scanning the LAG to create a mask image and several summary arrays that define and describe each CC.

The method to create an LAG in phase a) above is based on the description in the book "Algorithms for Graphics and Image Processing" by Pavlidis, Computer Science Press, 1982, pp. 116–120. It consists of, for each line of the thresholded image, finding runs of adjacent non-zero valued pixels, comparing the position of the runs on the current and prior adjacent line, and recording any overlap.

Although the LAG specifies which lines overlap, it does not define a connected component. Thus in phase b), each record of overlapping runs is scanned to determine to which CC each run belongs. Along the way, the total number of connected components is computed.

Figure 4:
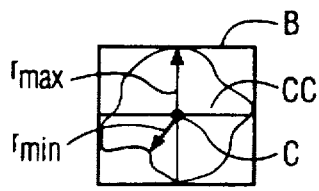
FIG. 4 shows a connected component extracted in a step of FIG. 2.

Once the set of CC's is known, then in phase c) a mask image and several data objects to define each CC are computed. The mask image is essentially the thresholded image in which all non-zero pixels contain the number of the CC to which they belong. The additional data objects include an array defining a bounding box B (minimum and maximum column and row) for each CC. A CC and its bounding box B are shown in FIG. 4.

After the extraction of connected components in step 40, an initial set of five relatively computationally inexpensive feature measures is calculated individually for each CC in step 42. Of this initial set, preferably, the variance measure Var of the intensities of the pixels in each CC is calculated first in accordance with the following equation:

$$Var = \frac{1}{n} \sum_{i=1}^{n} (g_i - \mu)^2$$

where $g_i$ is the gray value at location i, $\mu$ is the sample mean for the gray values of the pixels in the CC and n is their number. Thereafter the connected components are smoothed by erosion and then dilation. Preferably a structuring element which is a 3 by 3 matrix of ones is used for the erosion and the dilation. As a result, sharp irregularities in the boundaries of the connected regions are smoothed and small voids in their interiors are filled. Then the other four feature measures are calculated for each smoothed CC, namely area (Area), compactness (Compact), contrast (Contrast) and eccentricity (Ecc).

The compactness measure Compact is computed for each CC as follows:

$$Compact = \frac{P^2}{A}$$

where P is the perimeter and A is the area (Area) of the CC. This measure is minimum for a circle.

The contrast measure Contrast is calculated by subtracting the average gray value in a ring outside the connected component from the average gray value inside the connected component. The ring is obtained by dilating the connected components, then keeping only the new pixels.

The eccentricity measure Ecc is calculated as follows:

$$Ecc = \frac{r_{max}}{r_{min}}$$

where, as shown in FIG. 4, $r_{max}$ and $r_{min}$ are the maximum and minimum distances between the center of bounding box B and the perimeter of the CC.

Then, the calculated initial set of feature measures is applied to a multiple-rule based first classification stage 44 to identify candidate suspect masses from among the CC's. The operational phase of this stage is best understood by first discussing its training phase.

The training phase for first classification stage 44 as shown in FIG. 4A utilizes a set of training images in which regions of interest (roi's) corresponding to actual true positives have been marked by a radiologist. Satisfactory results have been obtained with a training set of 43 images.

In the first step 54 of this training phase, images are interactively segmented to extract areas (CC's) that match the radiologist's markings. This step involves interactive choice of a range of threshold levels which discriminate the marked CC's. Then in step 56, the initial met of five feature measures (Var, Area, Compact, Contrast and Ecc) is calculated for each extracted CC in the same manner as in step 42 of FIG. 2. The initial set of feature measures for each CC may be viewed as a point for each CC mapped in a Five-dimensional initial feature space. Then, in step 58, a K-means clustering is performed to cluster these CC's in initial feature space into k clusters, where k is empirically determined such that no cluster is contains only a very few points. The K-means algorithm in well known, e.g. from the book Hartigan, "Clustering Algorithm", John Wiley & Sons, 1975, Chapter 4. Each hyper-rectangle that encloses a cluster is used to devise a separate rule of the form:

(Area$\leq$Area$_{max}$) AND (Area$\geq$Area$_{min}$) AND (Compact$\leq$Compact$_{max}$) AND (Contrast$\geq$Contrast$_{min}$) AND (Ecc$\leq$Ecc$_{max}$) AND (Var$\leq$Var$_{max}$).

Figure 2:
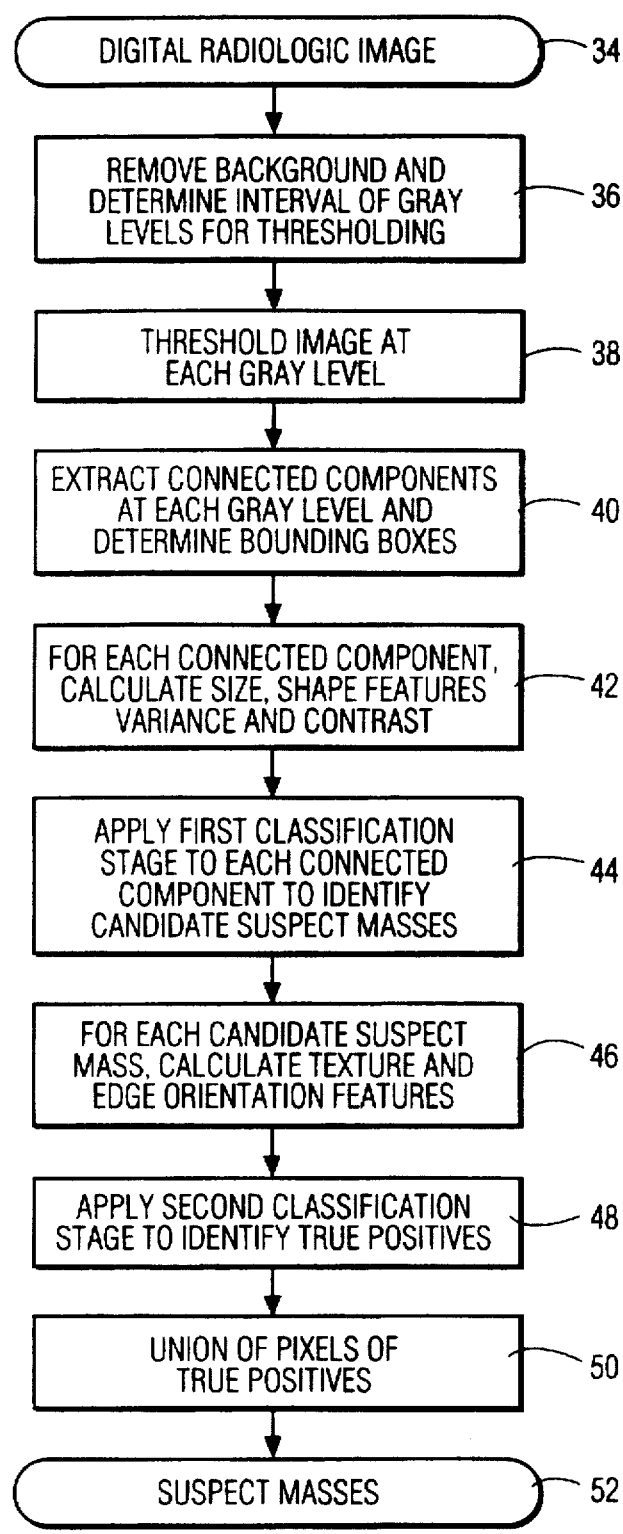
FIG. 2 is a flow chart indicating the processing performed by a computer in FIG. 1 in an operational phase.

These rules are used in the first classification phase 44 of FIG. 2, such that a connected component is accepted as a candidate suspect mass if its initial set of feature measures satisfies any of the k rules.

A typical set of rules for k=8 clusters uses the limit values summarized in the following table:

| k | Area$_{max}$ | Area$_{min}$ | Compact$_{max}$ | Contrast$_{min}$ | Ecc$_{max}$ | Var$_{max}$ |
|---|---|---|---|---|---|---|
| 1 | 900 | none | 20 | 4 | 2.3 | 50 |
| 2 | 2500 | none | 25 | 4 | 2.8 | 35 |
| 3 | 650 | 350 | 20 | 12 | 3.8 | 50 |
| 4 | 650 | none | 20 | 2 | 3.8 | 50 |
| 5 | 2300 | 260 | 27 | 7 | 3.6 | 10 |
| 6 | 1500 | 600 | 25 | 10 | 2.6 | 125 |
| 7 | 650 | 450 | 27 | 9 | 5.2 | 20 |
| 8 | none | 2000 | 27 | 3 | 2.9 | 50 |

In step 46 of FIG. 2, five more computationally expensive further feature measures are calculated, namely edge orientation and four Laws texture features to augment the initial set of five feature measures to an expanded set of ten feature measures. The edge orientation feature was generally suggested in Kegelmeyer, Evaluation of Stellate Lesion detection in a Standard Mammogram Data Set", International Journal of Pattern Recognition and Artificial Intelligence, Vol. 7, no. 6, pp. 1477-1492, 1993, based on modeling the architecture distortion caused by stellate lesions, where the tumor is surrounded by spicules. In the region around the tumor, edges will have many different orientations. Because a normal mammogram has a duct structure which radiates from the nipple, normal areas will have edges with similar orientations. This feature measure is calculated by computing edge orientation at each pixel in the bounding box B for the candidate suspect mass. Then the histogram of the edge orientations is computed and its flatness is measured by computing standard deviation of the edge orientation distribution. This manner of calculation differs from Kegelmeyer, where a window of fixed size is centered about each pixel in the image and edge orientation computed for pixels in the window. The present invention differs because its window size changes according to the size of the candidate suspect mass. Hence, the window will always contain the entire candidate suspect mass and will give a much more relevant measure.

The Laws texture features are calculated by convolving the image with a set of four 5×5 kernels designed to respond to different local behaviors, followed by measuring various statistics on the convolution images. These kernels are chosen as suggested in K.I. Laws, "Textured Image Segmentation", Ph.D. thesis, University of Southern California, 1980, wherein they are named E5L5, R5R5, E5S5, L5S5, (which are shown in FIGS. 6A–6D, respectively) followed by computation of the local average of absolute values. Preferably, according to the method of the present invention, these measures are normalized by the kernel L5L5, shown in FIG. 6E and the normalized sum is computed solely for the pixels in the bounding box B for the candidate suspect mass.

Figure 5A:
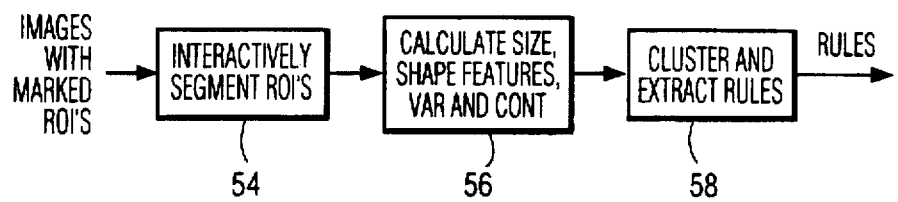
FIGS. 5A and 5B are flow charts indicating the training of first and second classification stages of FIG. 2, respectively.
Figure 5B:
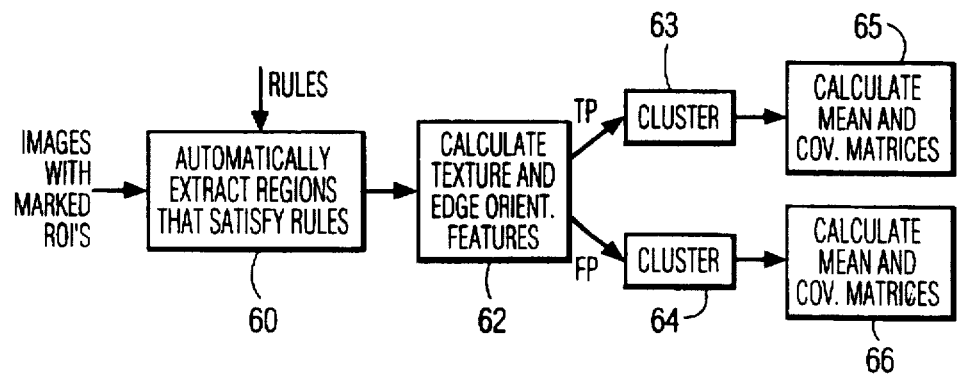

The expanded set of ten feature measures is applied to the second stage of classification in step 48 to separate the candidate suspect masses into true positives and false positives based on their proximity in feature space to true positives and false positives mapped in a training phase shown in FIG. 5B.

Since manses have different types with different characteristics and false positives can arise due to different reasons, it is expected that a single cluster in expanded feature space containing all the true positives of the training sample will tend to overlap a single cluster containing all the false positives of the training sample. Hence determining proximity of a point in ten-dimensional expanded feature space corresponding to a candidate suspect mass to the mean of the single cluster of true positives and to the mean of the single cluster of false positives would not be useful. On the other extreme, treating each of the true positives and each of the false positives mapped in the training phase as a separate class, as by a KNN (k-nearest neighbor) method would be quite time consuming because it would require the calculation and sorting of the distances to all points mapped from the training sample.

In accordance with the present invention, the true positives and false positives obtained as indicated in the succeeding paragraphs, are each separately clustered into an empirically determined plurality of clusters or subclasses. This reduces their overlap, and hence allows for better separation between true positives and false positives.

During the training phase for the second stage of classification, the steps 36 through 44 of FIG. 2 are applied to the entire training set of images, including as indicated in step 60 of FIG. 5B, the extraction of regions which satisfy any of the rules developed in the training phase for the first classification phase, shown in FIG. 5A. Then in step 62, as in step 46, the texture and edge orientation features are calculated to form an expanded set of feature measures for each extracted region. The resultant points in expanded feature space are segmented into true positives (TP) and false positives (FP) based on the radiologist's markings and they are separately clustered in steps 63 and 64 into a plurality of clusters. As with the clustering performed with regard to the training phase for the first classification stage shown in FIG. 5A, the K-means algorithm is used (although other clustering approaches are possible, and the number of clusters is chosen empirically so that no cluster contains only a few points.

Then, for each of the plurality of clusters, the mean and covariance matrix is calculated. The covariance matrix of a cluster is defined as:

$$\Sigma E[(\vec{X}-\vec{\mu})(\vec{X}-\vec{\mu})']$$

where the expected value of a matrix is found by taking the expected values of its components. Here, $\vec{X}$ is a ten (or in general, d) component column vector of data values and $\vec{\mu}$ is a ten (in general, d) component column vector of mean values.

In the operational phase of the second classification stage 48 of FIG. 2, the Mahalanobis distance from a point in expanded feature space corresponding to a candidate suspect mass is measured to the mean of each cluster of true positives of the training set and to the mean of each cluster of false positives of the training set and the candidate suspect mass is classified as the same class as the cluster whose mean is nearest in Mahalanobis distance. That is, if the mean of a cluster of true positives is nearest, the candidate suspect mass is classified as a true positive, whereas if the mean of a cluster of false positives is nearest, it is classified as a false positive. Mahalanobis distance $r_i$ from the $i^{th}$ cluster is defined as:

$$r_i \cdot \sqrt{(X - \mu_i)^\tau \Sigma_i^{-1} (X - \mu_i)}$$

where $\Sigma_i^{-1}$ is the inverse of the covariance matrix for the ith cluster, $\vec{X}$ is the feature vector in expanded feature space for the candidate suspect mass, and $\vec{\mu}_i$ is the mean of the $i^{th}$ cluster.

Lastly, in step 50, pixels belonging to a detected true positive are assigned the value binary one, and in order to reconcile duplicate detections of the same masses at different threshold levels, a binary mask is formed am the union of these binary pixels. The pixels in said mask having the value binary one belong to suspect masses 52 which are to be highlighted in the display 32.

The algorithm presented here was trained on a training set of 43 images which had been marked by a radiologist. Thereafter, the operational phase was tested on a test set of 81 images which also had been marked. Excluding 7 hard cases, the algorithm detected all the malignant masses in the test set with an average of 2.8 false positives detected per image. Since some images were different views of the same breast (cranio-caudal and oblique), the true positive detection rate was in excess of 90% when a true positive detection was counted if it occurred in either view.

While the present invention has been described in particular detail, it should be appreciated that numerous modifications are possible within the intended spirit and scope of the invention, which is defined in the appended claims.

What is claimed is:

1. A computer-implemented method of identifying suspect masses in a stored input two-dimensional array of digital pixels derived from an output of a radiologic imaging apparatus comprising:
   a) thresholding at least a portion of the pixels of the stored input array to discriminate spots;
   b) for each spot discriminated, in a first classification stage identifying whether said spot is a candidate suspect mass by:
      i) computing an initial set of feature measures of said spot, including measures of shape and size, constituting a location in an initial feature space, and
      ii) determining whether the computed initial set satisfies predetermined criteria; and
   c) for each spot identified as a candidate suspect mass, in a second classification stage determining whether said spot is a true positive suspect mass or a false positive suspect mass by:
      i) computing further feature measures to form an expanded set of feature measures constituting a location in an expanded feature space, and
      ii) comparing said location with predetermined locations in expanded feature space corresponding to true positives and corresponding to false positives by finding which predetermined location is nearest to the location of the spot, using a distance measure.

2. A method as claimed in claim 1, wherein said predetermined locations in expanded feature apace corresponding to true positives and to false positives comprise a plurality of predetermined locations corresponding to true positives and a plurality of predetermined locations corresponding to false positives.

3. A method as claimed in claim 1, wherein said predetermined criteria comprise a plurality of rules organized such that a spot is identified as a candidate suspect mass if its set of feature measures satisfies any of the plurality of rules.

4. A method as claimed in claim 2 wherein said predetermined criteria comprise a plurality of rules organized such that a spot is identified as a candidate suspect mass if its set of feature measures satisfies any of the plurality of rules.

5. A method as claimed in claim 2, wherein each location of said plurality of predetermined locations of true positives is determined from a different cluster of a plurality of clusters of true positives developed in a training phase for said first classification stage and each location of said plurality of predetermined locations of false positives is determined from a different cluster of a plurality of clusters of false positives developed in said training phase.

6. A method as claimed in claim 4, wherein each location of said plurality of predetermined locations of true positives is determined from a different cluster of a plurality of clusters of true positives developed in a training phase for said first classification stage and each location of said plurality of predetermined locations of false positives is determined from a different cluster of a plurality of clusters of false positives developed in said training phase.

7. A method as claimed in claim 3, wherein each rule of said plurality of rules is devised from a different cluster of a plurality of clusters of suspect masses in initial feature space developed in a training phase for said first classification stage.

8. A method as claimed in claim 4, wherein each rule of said plurality of rules is devised from a different cluster of a plurality of clusters of suspect masses in initial feature space developed in a training phase for said first classification stage.

9. A method as claimed in claim 6, wherein each rule of said plurality of rules is devised from a different cluster of a plurality of clusters of suspect masses in initial feature space developed in a training phase for said first classification stage.

10. A method as claimed in claim 1, wherein said further feature measures of a spot include a plurality of texture feature measures computed based solely on intensities of pixels within a bounding box, each of whose sides adjoin an edge of the spot.

11. A method as claimed in claim 2, wherein said further feature measures of a spot include a plurality of texture feature measures computed based solely on intensities of pixels within a bounding box, each of whose sides adjoin an edge of the spot.

12. A method as claimed in claim 3, wherein said further feature measures of a spot include a plurality of texture feature measures computed based solely on intensities of pixels within a bounding box, each of whose sides adjoin an edge of the spot.

13. A method as claimed in claim 1, wherein said further feature measures include a measure of edge gradient orientation distribution.

14. A method as claimed in claim 2, wherein said further feature measures include a measure of edge gradient orientation distribution.

15. A method as claimed in claim 3, wherein said further feature measures include a measure of edge gradient orientation distribution.

16. A method as claimed in claim 10, wherein said further feature measures include a measure of edge gradient orientation distribution.

17. A method an claimed in claim 1, wherein said thresholding is at, at least, 20 different threshold levels.

18. A method as claimed in claim 2, wherein said thresholding is at, at least, 20 different threshold levels.

19. A method as claimed in claim 1, wherein said distance measure is Mahalanobis distance.

20. A system for producing a computer-enhanced radiologic image comprising:

means including an X-ray source, for irradiating a region of a body being examined with X-ray radiation in a predetermined viewing directions;

means for receiving the X-ray radiation exiting the region from said viewing direction within a two-dimensional field;

means for producing digital signals as a function of the X-ray radiation received, which digital signals correspond to an input two-dimensional array of digital pixels;

a computer;

a digital memory means accessible to said computer;

means for, in response to said signals, storing said input two-dimensional array of digital pixels in said digital memory means;

wherein said computer is configured for processing the stored input two-dimensional array or digital pixels by:

a) thresholding at least a portion of the pixels of the stored input array to discriminate spots;

b) for each spot discriminated, in a first classification stage identifying whether said spot is a candidate suspect mass by:

i) computing an initial set of feature measures of said spot, including measures of shape and size, constituting a location in an initial feature space, and ii) determining whether the computed initial set satisfies predetermined criteria; and c) for each spot identified as a candidate suspect mass, in a second classification stage determining whether said spot is a true positive suspect mass or a false positive suspect mass by;

i) computing further feature measures to form an expanded set of feature measures constituting a location in an expanded feature space, and ii) comparing said location with predetermined locations in expanded feature space corresponding to true positives and corresponding to false positives by finding which predetermined location is nearest to the location of the spot, using a distance measure.

\* \* \* \* \*